(12) United States Patent
Tsai et al.

(10) Patent No.: US 10,258,475 B2
(45) Date of Patent: Apr. 16, 2019

(54) FEMUR SUPPORTING DEVICE

(71) Applicant: METAL INDUSTRIES RESEARCH & DEVELOPMENT CENTRE, Kaohsiung (TW)

(72) Inventors: Tung-Lin Tsai, Kaohsiung (TW); Chia-Lung Li, Kaohsiung (TW); Shih-Hua Huang, Kaohsiung (TW); Pei-Hua Wang, Kaohsiung (TW); Chun-Chieh Tseng, Kaohsiung (TW); Yue-Jun Wang, Kaohsiung (TW); Li-Wen Weng, Kaohsiung (TW)

(73) Assignee: Metal Industries Research & Development Centre, Kaohsiung (TW)

( * ) Notice: Subject to any disclaimer, the term of this patent is extended or adjusted under 35 U.S.C. 154(b) by 64 days.

(21) Appl. No.: 15/585,266

(22) Filed: May 3, 2017

(65) Prior Publication Data

US 2018/0055646 A1    Mar. 1, 2018

(30) Foreign Application Priority Data

Aug. 23, 2016   (TW) .............................. 105126938 A

(51) Int. Cl.
*A61F 2/36*        (2006.01)
*A61B 17/74*       (2006.01)
(Continued)

(52) U.S. Cl.
CPC .......... *A61F 2/3609* (2013.01); *A61B 17/744* (2013.01); *A61B 17/746* (2013.01); *A61F 2/367* (2013.01); *A61F 2002/30405* (2013.01); *A61F 2002/30433* (2013.01); *A61F 2002/30784* (2013.01); *A61F 2002/365* (2013.01); *A61F 2002/3613* (2013.01);
(Continued)

(58) Field of Classification Search
CPC ...... A61F 2002/3613; A61F 2002/3621; A61F 2002/368; A61F 2002/3682; A61F 2002/3684; A61B 17/746
USPC ............................................ 623/23.26, 23.27
See application file for complete search history.

(56) References Cited

U.S. PATENT DOCUMENTS 8,157,803 B1 *   4/2012   Zirkle, Jr. ............ A61B 17/746
                                                                606/64

FOREIGN PATENT DOCUMENTS

TW        I305722 B      2/2009
TW        I312677 B      8/2009
(Continued)

*Primary Examiner* — David H Willse
(74) *Attorney, Agent, or Firm* — Alan D. Kamrath; Kamrath IP Lawfirm, P.A.

(57) ABSTRACT

A femur supporting device includes a femoral stem having a plurality of inclined passages. The femoral stem includes an inner side and an outer side. Each inclined passage includes an outlet in the inner side and an inlet in the outer side. Each inclined passage inclines upward from the inlet to the outlet. A plurality of supporting rods extends through the inclined passages. A first engaging end of each supporting rod extends out of the outlet of one of the inclined passages. A second engaging end of each supporting rod extends out of the inlet of one of the inclined passages. The first engaging end of each supporting rod is engaged with one of a plurality of first engaging portions in a trochanter head. The second engaging end of each supporting rod is engaged with one of a plurality of second engaging portions of a fixing unit.

9 Claims, 5 Drawing Sheets

(51) Int. Cl.
 *A61B 17/76* (2006.01)
 *A61F 2/30* (2006.01)
(52) U.S. Cl.
 CPC ............... *A61F 2002/3625* (2013.01); *A61F 2002/3652* (2013.01); *A61F 2002/3684* (2013.01)

(56) References Cited

FOREIGN PATENT DOCUMENTS

| | | |
|---|---|---|
| TW | M389530 | 10/2010 |
| TW | M394805 U | 12/2010 |

\* cited by examiner

FEMUR SUPPORTING DEVICE

CROSS REFERENCE TO RELATED APPLICATIONS

The application claims the benefit of Taiwan application Ser. No. 105126938, filed on Aug. 23, 2016, and the entire contents of which are incorporated herein by reference.

BACKGROUND OF THE INVENTION

1. Field of the Invention

The present invention relates to an orthopedic medical apparatus and, more particularly, to a femur supporting device to be mounted in a femur for cooperating with an acetabular cup to form an artificial hip joint.

2. Description of the Related Art

FIG. 1 shows a conventional femur supporting device 9 including a seat 91, a stem 92, and an inclined post 93. The stem 92 includes a handle end 921 and a joint end 922. An end of the inclined post 93 is integrally connected to the joint end 922 of the stem 92. In assembly, the handle end 921 of the stem 92 extends through the seat 91, and the seat 91 is engaged at a location adjacent to the joint end 922 to securely position the stem 92.

When it is desired to implant the conventional femur supporting device 9 into a human body, the muscle and ligament enveloping a femur F are cut open first, and the femoral neck and the femoral head are removed by cutting. Then, the cancellous bone of the femur F is drilled to form a hole for implantation of the conventional femur supporting device 9. After implantation of the conventional femur supporting device 9 into the femur F, the inclined post 93 extends obliquely beyond the femur F of the patient to replace the femoral neck. An acetabular unit (not shown) can be coupled to a free end of the inclined post 93.

However, the conventional femur supporting device 9 withstands the vertical stress of the body and the oblique torque of the femoral trochanter by a single inclined post 93, which is difficult to effectively disperse the load. Thus, the conventional femur supporting device 9 is apt to malfunction after a period of time.

Furthermore, the inclined post 93 is integrally connected to the stem 92, such that it is impossible to change the length of the stem 92 or the inclined post 93 according to the shape of the bone of the patient and impossible to adjust the inclination angle between the inclined post 93 and the stem 92. Thus, it is necessary to manufacture conventional femur supporting devices 9 of many specifications for selective use, which is very inconvenient to material management for hospitals and causes inventory pressure to the manufacturers. Furthermore, the conventional femur supporting device 9 of each specification contains the whole stem 92 and the whole inclined post 93, which consumes a large quantity of material, results in high costs, and requires considerable space for inventory.

An example of the above conventional femur supporting device 9 has been disclosed in Taiwan Patent No. I312677 entitled "Artificial Femoral Structure". Taiwan Utility Model No. M394805 entitled "Femoral Prothesis", Taiwan Utility Model No. M389530 entitled "Antibiotic-Containing Bone Cement Femoral Supporting Device with High Resistance to Pressure", and Taiwan Patent No. I305722 entitled "Artificial Bone with Porous Tissue" disclose similar structures and, thus, have the same disadvantages.

Thus, improvement to conventional femur supporting devices is necessary.

SUMMARY OF THE INVENTION

To solve the above disadvantages, the present invention provides a femur supporting device including a plurality of supporting rods to jointly withstand the trochanter head and the acetabular cup, effectively dispersing the load.

The present invention provides a femur supporting device including modularized components that can be assembled to form a femur supporting device most suitable to the shape of the bone of the patient.

When the terms "up", "down", "distal end", "proximal end", "inner side", "outer side", and similar terms are used herein, it should be understood that these terms have the same definitions used in anatomy. Namely, "upper" refers to the side proximal to the head, "lower" refers to the side proximal to the sole, "distal end" refers to distant to the root of the torso, "proximal end" refers to adjacent to the root of the torso, and "inner side" and "outer side" are decided according to the relative distance to the median sagittal plane of the human body.

A femur supporting device according to the present invention includes a femoral stem having a plurality of inclined passages. The femoral stem includes an inner side and an outer side. Each of the plurality of inclined passages includes an outlet in the inner side and an inlet in the outer side. Each of the plurality of inclined passages inclines upward from the inlet to the outlet. A plurality of supporting rods extends through the plurality of inclined passages. Each of the plurality of supporting rods includes a first engaging end and a second engaging end. The first engaging end of each of the plurality of supporting rods extends out of the outlet of one of the plurality of inclined passages. The second engaging end of each of the plurality of supporting rods extends out of the inlet of one of the plurality of inclined passages. A trochanter head includes a plurality of first engaging portions. The first engaging end of each of the plurality of supporting rods is engaged with one of the plurality of first engaging portions. A fixing unit includes a plurality of second engaging portions. The second engaging end of each of the plurality of supporting rods is engaged with one of the plurality of second engaging portions.

Thus, the femur supporting device according to the present invention can be assembled to be of the most suitable arrangement based on the shape of the bone of the patient and can effectively disperse the load, achieving the therapy effect, prolonging the service life, increasing material management convenience for hospitals, reducing the inventory pressure to the manufacturers, and reducing the costs and storage space for products of various specifications. As a result, all the disadvantages of the integral type conventional femur supporting devices are solved.

In an example, the plurality of inclined passages includes at least three inclined passages. Each of the at least three inclined passages has a central axis. The central axes of any three of the at least three inclined passages are not located on the same plane. This structure permits the supporting rods to be disposed in a three dimensional manner to increase the supporting effect.

In an example, the first engaging end and the second engaging end of each of the plurality of supporting rods have an identical outline. This structure increases the assembling convenience.

In an example, the first engaging portions of the trochanter head are arranged annularly. The number of the plurality of first engaging portions of the trochanter head is larger than the number of the supporting rods. Thus, the trochanter head is universal.

In an example, the fixing unit includes a fixing board and a plurality of pressing members. The fixing board includes a plurality of through-holes. The plurality of second engaging portions is disposed on the plurality of pressing members, respectively. The second engaging end of each of the plurality of supporting rods extends through one of the plurality of through-holes and is engaged with one of the plurality of second engaging portions on one of the plurality of pressing members. Thus, the plural supporting rods are fixed by a simple structure, and the fixing unit is easy to manufacture and assemble, reducing the manufacturing costs and increasing the assembling convenience.

In an example, the fixing board includes a central hole, and the plurality of through-holes is disposed around the central hole. This structure makes the fixing board difficult to break.

In an example, the fixing board includes a plurality of channels. Each of the plurality of channels extends from the central hole to an outer periphery of the fixing board and is located between two adjacent through-holes. This structure further increases the structural strength of the fixing board.

In an example, the second engaging end of each of the plurality of supporting rods includes an outer thread. Each of the plurality of second engaging portions is a screw hole having an inner thread and is in a form of a blind hole. This structure increases the assembling convenience of the trochanter head and the fixing unit, is easy to process for formation, and reduces the manufacturing costs while avoiding the second engaging member of each supporting rod from extending out of the corresponding pressing member to scratch the operator or the tissue adjacent to the femur of the patient, thereby increasing the use safety.

In an example, each of the plurality of pressing members includes a round face. This structure further increases the use safety of the pressing members.

In an example, the inner thread of each of the plurality of second engaging portions has a length larger than a length of the outer thread of the second engaging end of each of the plurality of supporting rods. This structure increases the stability of locking and positioning.

In an example, the number of the plurality of through-holes of the fixing board is larger than the number of the plurality of supporting rods to make the fixing board universal.

The present invention will become clearer in light of the following detailed description of illustrative embodiments of this invention described in connection with the drawings.

DETAILED DESCRIPTION OF THE INVENTION

Figure 1:
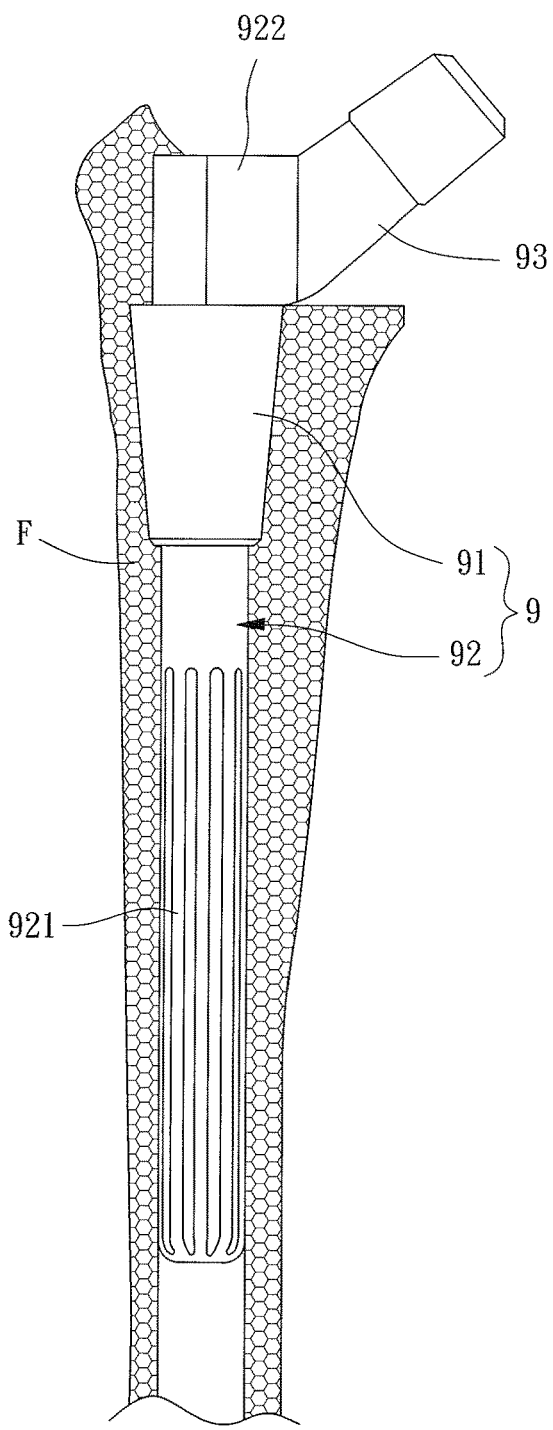
FIG. 1 is a diagrammatic cross sectional view of a conventional femur supporting device.
Figure 2:
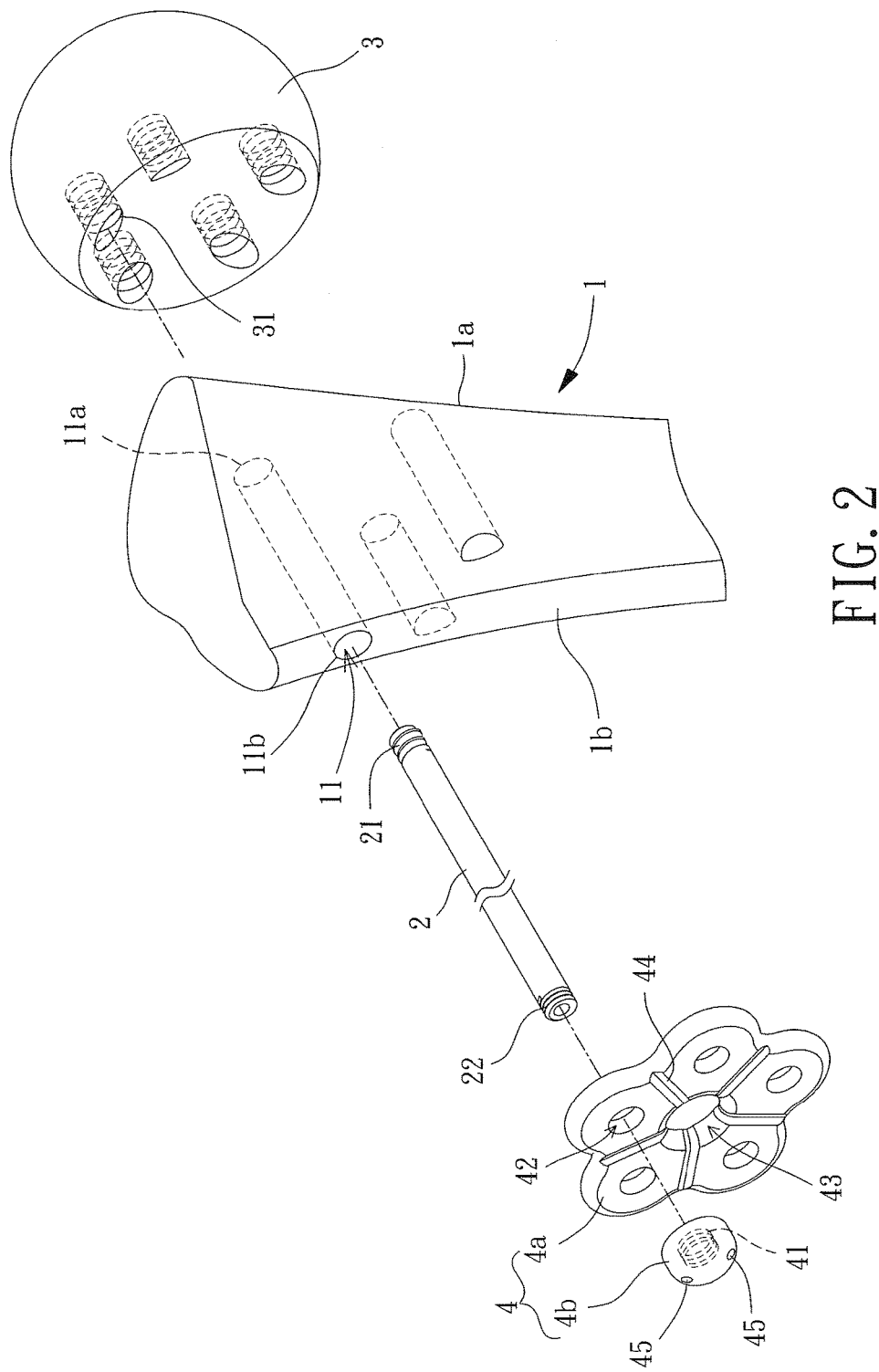
FIG. 2 is an exploded, perspective view of a femur supporting device of an embodiment according to the present invention.
Figure 3:
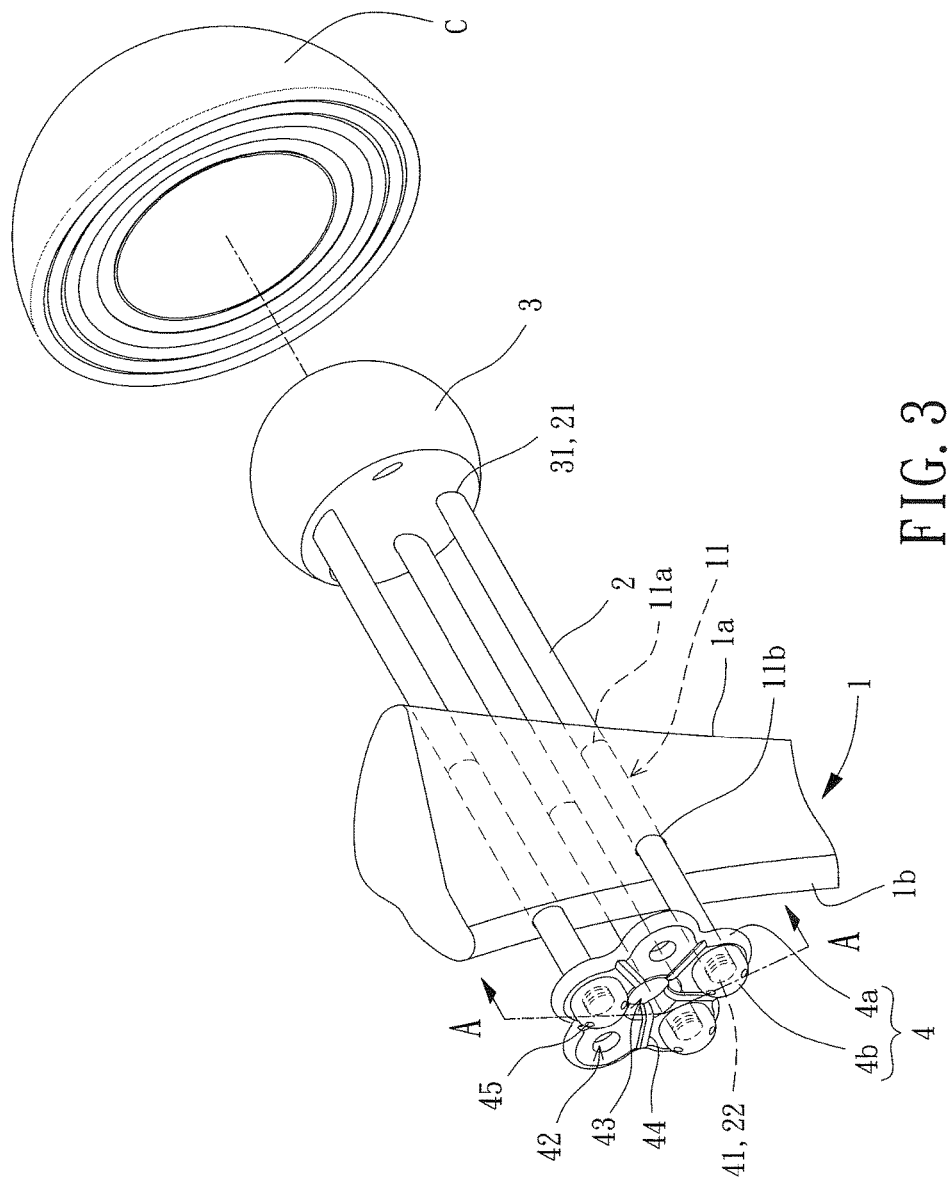
FIG. 3 is a diagrammatic perspective view illustrating use of the femur supporting device of FIG. 2 with an acetabular cup.

FIGS. 2 and 3 show a femur supporting device of an embodiment according to the present invention. The femur supporting device generally includes a femoral stem 1, a plurality of supporting rods 2, a trochanter head 3, and a fixing unit 4. The supporting rods 2 extend through the femoral stem 1. Two ends of each supporting rod 2 are respectively engaged with the trochanter head 3 and the fixing unit 4.

Figure 4:
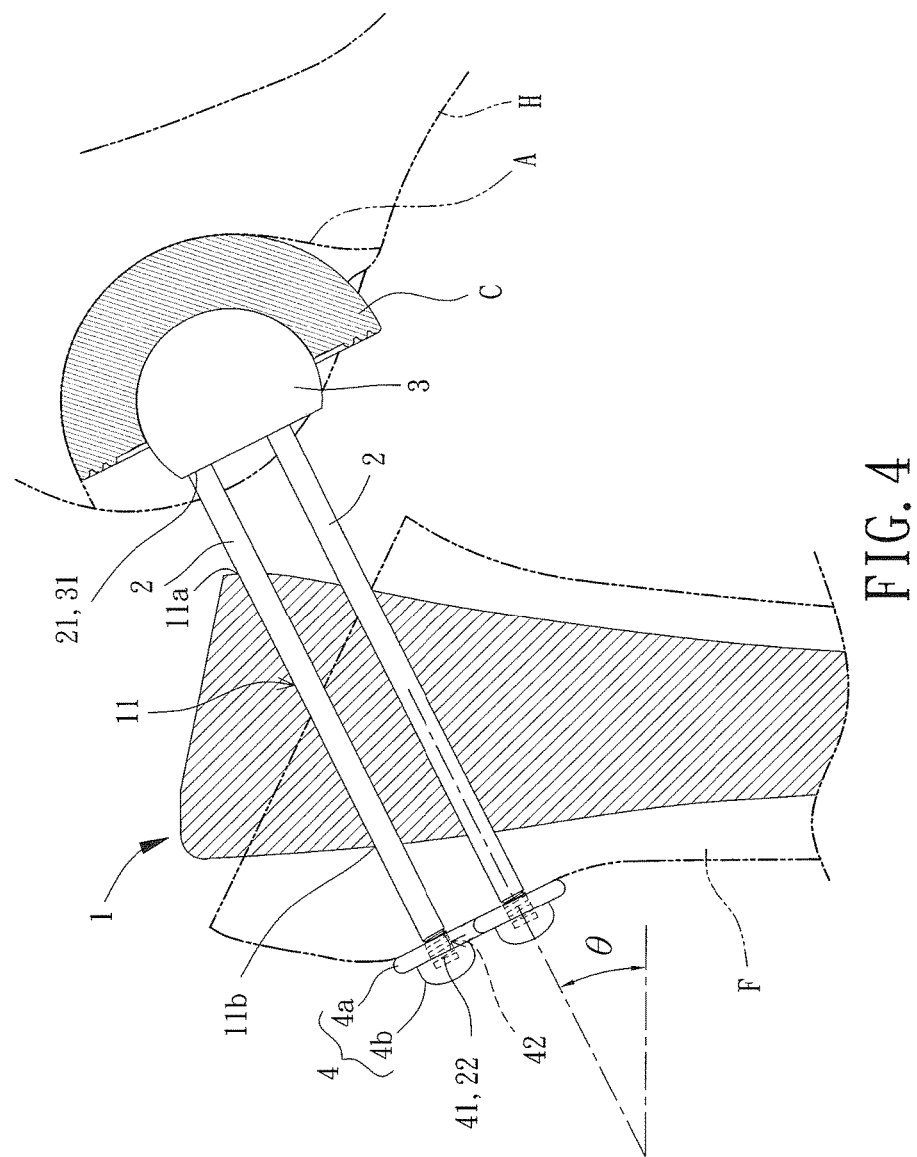
FIG. 4 is a cross sectional view taken along section line A-A of FIG. 3, illustrating an example of use of the femur supporting device of an embodiment according to the present invention.
Figure 5:
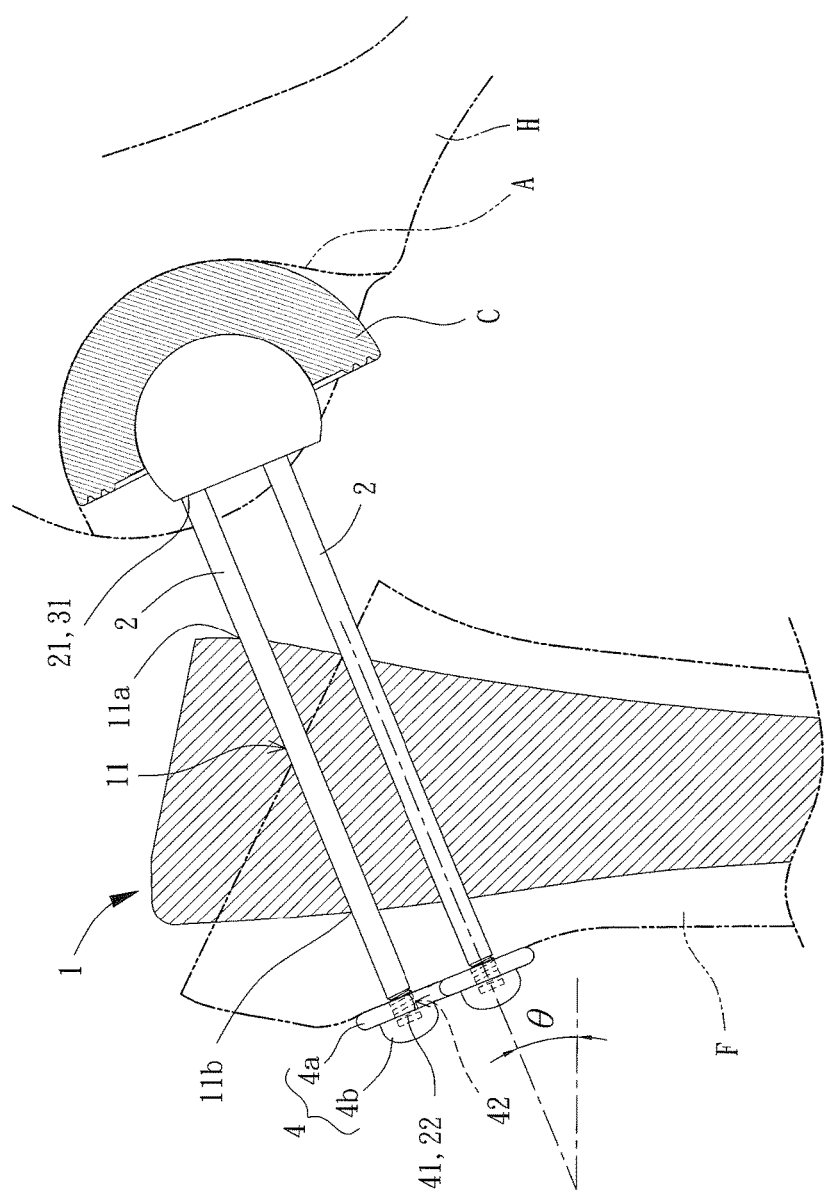
FIG. 5 is a cross sectional view taken along section line A-A of FIG. 3, illustrating another example of use of the femur supporting device of an embodiment according to the present invention.

With reference to FIGS. 2 and 4, the femoral stem 1 is an elongated stem for implantation into a bone marrow cavity of a femur F. Preferably, the femoral stem 1 has a rough outer surface to provide a better biological bonding effect. The femoral stem 1 includes an inner side 1a and an outer side 1b. After the femoral stem 1 has been implanted into the femur F of a patient, the inner side 1a of the femoral stem 1 is closer to the acetabulum A of the hip bone H of the patient than the outer side 1b. The femoral stem 1 includes a plurality of inclined passages 11. Each inclined passage 11 includes an outlet 11a in the inner side 1a and an inlet 11b in the outer side 1b. Each inclined passage 11 inclines upward from the inlet 11b to the outlet 11a. Each inclined passage 11 includes a central axis at an angle $\theta$ to a horizontal plane. Femoral stems 1 of different specifications can have inclined passages 11 of different angles $\theta$ to permit an operator to choose a suitable femoral stem 1 according to the inclination degree of the original femoral neck of the patient.

Still referring to FIGS. 2 and 3, each supporting rod 2 includes a first engaging end 21 and a second engaging end 22. The supporting rods 2 respectively extend through the inclined passages 11. The first engaging end 21 of each supporting rod 2 extends out of the outlet 11a of one of the inclined passages 11 for engaging with the trochanter head 3. The second engaging end 22 of each supporting rod 2 extends out of the inlet 11b of one of the inclined passages 11 for engaging with the fixing unit 4. Thus, the present invention can support the trochanter head 3 by the supporting rods 2 to effectively disperse the load. The number of the inclined passages 11 of the femoral stem 1 is not limited. Preferably, the femoral stem 1 includes at least three inclined passages. Each of the at least three inclined passages 11 has a central axis. The central axes of any three of the at least three inclined passages 11 are not located on the same plane. Thus, the supporting rods 2 extending through the inclined passages 11 are disposed in a three dimensional manner to provide a better positioning effect for the trochanter head 3.

The first and second engaging ends 21 and 22 of the supporting rods 2 are not limited in structure as long as the first and second engaging ends 21 and 22 can engage with the trochanter head 3 and the fixing unit 4, respectively. The first engaging end 21 and the second engaging end 22 of each supporting rod 2 can have an identical outline, such that either end of each supporting rod 2 can be inserted into the body of the patient without causing errors in the assembling direction, thereby increasing the assembling convenience. In a non-restrictive example, each of the first engaging end 21 and the second engaging end 22 of each supporting rod 2 includes an outer thread to permit easy assembly with and detachment from the trochanter head 3 and the fixing unit 4 and are, thus, easy to process for formation, which is helpful in reducing the manufacturing costs. Alternatively, the first engaging end 21 and the second engaging end 22 of each supporting rod 2 can have structures that cannot be separated without destruction after engagement, such that the first and second engaging ends 21 and 22 of each supporting rod 2 can be securely engaged with the trochanter head 3 and the fixing unit 4. In another example, the first engaging end 21 and the second engaging end 22 of each supporting rod 2 have different structures to meet different engagement needs.

The trochanter head 3 includes a plurality of first engaging portions 31. The first engaging end 21 of each supporting rod 2 is engaged with one of the first engaging portions 31. The first engaging portions 31 of the trochanter head 3 are arranged annularly. Preferably, the number of the first engaging portions 31 of the trochanter head 3 is larger than the number of the supporting rods 2. Thus, the trochanter head 3 is universal and can be used regardless of the number of the supporting rods 2 and regardless whether the supporting rods 2 are spaced by regular or irregular intervals. In this embodiment, each first engaging portion 31 is a screw hole having an inner thread for matching with the first engaging end 21 in the form of an outer thread.

With reference to FIGS. 2 and 4, the fixing unit 4 includes a plurality of second engaging portions 41. The second engaging end 22 of each supporting rod 2 is engaged with one of the second engaging portions 41 to fix the second engaging ends 22 of the supporting rod 2 to an outer side of the femur F. In this embodiment, the fixing unit 4 includes a fixing board 4a and a plurality of pressing members 4b. The fixing board 4a includes a plurality of through-holes 42. The second engaging portions 41 are disposed on the pressing members 4b, respectively. By such an arrangement, the second engaging end 22 of each supporting rod 2 extends through one of the through-holes 42 and is engaged with the second engaging portion 41 of one of the pressing members 4b. Thus, the fixing board 4a is fixed by the pressing members 4b to firmly abut the outer face of the femur F.

Preferably, the number of the through-holes 42 of the fixing board 4a is larger than the number of the supporting rods 2 to make the fixing board 4a universal. Furthermore, the fixing board 4a includes a central hole 43, and the through-holes 42 are disposed around the central hole 43. The stress at the through-holes 42 of the fixing board 4a can be absorbed by the central hole 43. Thus, the fixing board 4a does not break easily. Particularly, in this embodiment, the fixing board 4a further includes a plurality of channels 44. Each channel 44 extends from the central hole 43 to an outer periphery of the fixing board 4a and is located between two adjacent through-holes 42. Thus, a load at any position of the fixing board 4a can be more easily transmitted through the nearest channel 44 to the central hole 43, further increasing the structural strength of the fixing board 4a.

The second engaging portion 41 of each pressing member 4b can be a screw hole for rapid threading connection with the second engaging end 22 of one of the supporting rods 2 in the form of an outer thread. In this embodiment, the second engaging portion 41 of each pressing member 4b is in the form of a blind hole to avoid the second engaging end 22 of each supporting rod 2 from extending out of the corresponding pressing member 4b to scratch the operator or the tissue adjacent to the femur F of the patient. Preferably, each pressing member 4b includes a round face to further enhance use safety of the pressing member 4b. In this case, the outer surface of each pressing member 4b can include a plurality of insertion holes 45 permitting insertion of a tool for rotating the pressing member 4b. Furthermore, the length of the inner thread of the second engaging portion 41 of each pressing member 4b is preferably larger than the length of the outer thread of the second engaging end 22 of each supporting rod 2. Thus, the second engaging end 22 of each supporting rod 2 can be completely screwed into the corresponding pressing member 4b, such that the fixing board 4a and the femur F of the patient can be tightened through the corresponding member 4b, increasing the stability of locking and positioning.

With reference to FIGS. 3 and 4, according to the above structure, the femur supporting device according to the present invention can cooperate with an acetabular cup C to form an artificial hip joint. In use of the femur supporting device according to the present invention, the operator can select a femoral stem 1 having inclined passages 11 with the most suitable angle θ and a plurality of supporting rods 2 with the most suitable length based on the inclination degree and the length of the original femoral neck of the patient.

During operation, the operator extends a desired number of supporting rods 2 from an outer side of the femur F through the femur F and the femoral stem 1. The first engaging end 21 of each supporting rod 2 is engaged with one of the first engaging portions 31 of the trochanter head 3. Then, the trochanter head 3 is placed into the acetabular cup C, and the acetabular cup C is aligned with and inserted into the acetabulum A of the hip bone H. Next, the fixing board 4a of the fixing unit 4 abuts the outer side of the femur F, and the second engaging end 22 of each supporting rod 2 extends through one of the through-holes 42 of the fixing board 4a. Then, the second engaging portion 41 of each pressing member 4b is engaged with the second engaging end 22 of one of the supporting rods 2. Thus, the femur F and the acetabulum A of the patient can remain positioned by a fixed distance and a fixed angle. The operation of placement of an artificial hip joint is, thus, accomplished.

Since the plural supporting rods 2 of the femur supporting device according to the present invention jointly support the trochanter head 3 and the acetabular cup C, an artificial hip joint including the femur supporting device according to the present invention can effectively disperse and support the load including the vertical stress of the body and the oblique torque of the femoral trochanter, which not only reduces the time for recovery but reduces discomfort of the patient after placement of the artificial hip joint.

Furthermore, the femur supporting device according to the present invention can be dismantled into a plurality of components and, thus, permits selection of suitable components based on the shapes of the femurs F of different patients. The selected components can be assembled to form a femur supporting device according to the present invention most suitable for the patient receiving the operation. This reduces discomfort to the patient after placement of the artificial hip joint and increases the therapy effect and quality. Furthermore, the components can be dismantled for easy storage and management, increasing material management convenience for hospitals, reducing the inventory pressure to the manufacturers, and reducing the costs and storage space for products of various specifications.

As an example, as shown in FIG. 4, when the original femoral neck of the patient has a larger inclination angle and the femoral head has a shorter spacing to the outer side of the femur F, a femoral stem 1 including inclined passages 11 of a larger angle θ is selected to cooperate with a plurality of shorter supporting rods 2, such that the femur supporting device can match the original bone shape of the patient.

In view of the foregoing, the femur supporting device according to the present invention can be assembled to be of the most suitable arrangement based on the shape of the bone of the patient and can effectively disperse the load, achieving the therapy effect, prolonging the service life, increasing material management convenience for hospitals, reducing the inventory pressure to the manufacturers, and reducing the costs and storage space for products of various specifications. As a result, all the disadvantages of the integral type conventional femur supporting devices are solved.

Thus since the invention disclosed herein may be embodied in other specific forms without departing from the spirit or general characteristics thereof, some of which forms have been indicated, the embodiments described herein are to be considered in all respects illustrative and not restrictive. The scope of the invention is to be indicated by the appended claims, rather than by the foregoing description, and all changes which come within the meaning and range of equivalency of the claims are intended to be embraced therein.

What is claimed is:

1. A femur supporting device comprising:
   a femoral stem including a plurality of inclined passages, with the femoral stem including an inner side and an outer side, with each of the plurality of inclined passages including an outlet in the inner side and an inlet in the outer side, wherein each of the plurality of inclined passages inclines upward from the inlet to the outlet;
   a plurality of supporting rods extending through the plurality of inclined passages, with each of the plurality of supporting rods including a first engaging end and a second engaging end, with the first engaging end of each of the plurality of supporting rods extending out of the outlet of one of the plurality of inclined passages, and with the second engaging end of each of the plurality of supporting rods extending out of the inlet of one of the plurality of inclined passages;
   a trochanter head including a plurality of first engaging portions, with the first engaging end of each of the plurality of supporting rods engaged with one of the plurality of first engaging portions; and
   a fixing unit including a plurality of second engaging portions, with the second engaging end of each of the plurality of supporting rods engaged with one of the plurality of second engaging portions, wherein the fixing unit further includes a fixing board and a plurality of pressing members, wherein the fixing board includes a plurality of through-holes, wherein the plurality of second engaging portions is disposed on the plurality of pressing members, respectively, wherein the second engaging end of each of the plurality of supporting rods extends through one of the plurality of through-holes and is engaged with one of the plurality of second engaging portions on one of the plurality of pressing members, wherein the fixing board further includes a central hole, and wherein the plurality of through-holes is disposed around the central hole.

2. The femur supporting device as claimed in claim 1, wherein the plurality of inclined passages includes at least three inclined passages, wherein each of the at least three inclined passages has a central axis, and wherein the central axes of any three of the at least three inclined passages are not located on a same plane.

3. The femur supporting device as claimed in claim 1, wherein the first engaging end and the second engaging end of each of the plurality of supporting rods have an identical outline.

4. The femur supporting device as claimed in claim 1, wherein the plurality of first engaging portions of the trochanter head are arranged annularly, and wherein a number of the plurality of first engaging portions of the trochanter head is larger than a number of the plurality of supporting rods.

5. The femur supporting device as claimed in claim 1, wherein the fixing board includes a plurality of channels, wherein each of the plurality of channels extends from the central hole to an outer periphery of the fixing board and is located between two adjacent through-holes.

6. The femur supporting device as claimed in claim 1, wherein a number of the plurality of through-holes of the fixing board is larger than a number of the plurality of supporting rods.

7. A femur supporting device comprising:
   a femoral stem including a plurality of inclined passages, with the femoral stem including an inner side and an outer side, with each of the plurality of inclined passages including an outlet in the inner side and an inlet in the outer side, wherein each of the plurality of inclined passages inclines upward from the inlet to the outlet;
   a plurality of supporting rods extending through the plurality of inclined passages, with each of the plurality of supporting rods including a first engaging end and a second engaging end, with the first engaging end of each of the plurality of supporting rods extending out of the outlet of one of the plurality of inclined passages, and with the second engaging end of each of the plurality of supporting rods extending out of the inlet of one of the plurality of inclined passages;
   a trochanter head including a plurality of first engaging portions, with the first engaging end of each of the plurality of supporting rods engaged with one of the plurality of first engaging portions; and
   a fixing unit including a plurality of second engaging portions, with the second engaging end of each of the plurality of supporting rods engaged with one of the plurality of second engaging portions, wherein the fixing unit further includes a fixing board and a plurality of pressing members, wherein the fixing board includes a plurality of through-holes, wherein the plurality of second engaging portions is disposed on the plurality of pressing members, respectively, wherein the second engaging end of each of the plurality of supporting rods extends through one of the plurality of through-holes and is engaged with one of the plurality of second engaging portions on one of the plurality of pressing members, wherein the second engaging end of each of the plurality of supporting rods includes an outer thread, and wherein each of the plurality of second engaging portions is a screw hole having an inner thread and is in a form of a blind hole.

8. The femur supporting device as claimed in claim 7, wherein each of the plurality of pressing members includes a round face.

9. The femur supporting device as claimed in claim 7, wherein the inner thread of each of the plurality of second engaging portions has a length larger than a length of the outer thread of the second engaging end of each of the plurality of supporting rods.

* * * * *